(12) United States Patent
Tsukagoshi

(10) Patent No.: US 9,628,773 B2
(45) Date of Patent: Apr. 18, 2017

(54) IMAGE PROCESSING APPARATUS, IMAGE PROCESSING METHOD, AND MEDICAL IMAGE DIAGNOSIS APPARATUS

(75) Inventor: Shinsuke Tsukagoshi, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 937 days.

(21) Appl. No.: 13/540,939

(22) Filed: Jul. 3, 2012

(65) Prior Publication Data

US 2013/0176404 A1  Jul. 11, 2013

(30) Foreign Application Priority Data

Jul. 4, 2011  (JP) .................................. 2011-148579

(51) Int. Cl.
| | | |
|---|---|---|
| H04N 13/00 | (2006.01) | |
| H04N 13/02 | (2006.01) | |
| H04N 13/04 | (2006.01) | |
| A61B 6/02 | (2006.01) | |
| A61B 6/00 | (2006.01) | |
| A61B 5/00 | (2006.01) | |

(52) U.S. Cl.
CPC ............ *H04N 13/02* (2013.01); *A61B 6/022* (2013.01); *A61B 6/466* (2013.01); *H04N 13/007* (2013.01); *H04N 13/0055* (2013.01); *H04N 13/0275* (2013.01); *H04N 13/0402* (2013.01); *A61B 5/742* (2013.01); *A61B 6/468* (2013.01); *A61B 6/48* (2013.01); *A61B 6/503* (2013.01)

(58) Field of Classification Search
CPC ........... A61B 6/022; A61B 6/466; A61B 6/48; H04N 13/02; H04N 13/055

USPC ............................................................ 348/51
See application file for complete search history.

(56) References Cited

U.S. PATENT DOCUMENTS

| | | |
|---|---|---|
| 5,090,038 A | 2/1992 | Asahina |
| 2004/0097805 A1* | 5/2004 | Verard et al. ................ 600/428 |
| 2006/0039529 A1* | 2/2006 | Tsubaki et al. ................ 378/41 |
| 2006/0066718 A1* | 3/2006 | Yanagawa et al. ............ 348/51 |
| 2006/0232719 A1* | 10/2006 | Abileah .......................... 349/15 |
| 2007/0258632 A1 | 11/2007 | Friedman et al. |

(Continued)

FOREIGN PATENT DOCUMENTS

| | | |
|---|---|---|
| CN | 102045578 A | 5/2011 |
| JP | 9-218963 A | 8/1997 |

(Continued)

OTHER PUBLICATIONS

Chinese Office Action issued Mar. 25, 2014, in China Patent Application No. 201210224319.3.

(Continued)

*Primary Examiner* — Jeffrey Williams
(74) *Attorney, Agent, or Firm* — Oblon, McClelland, Maier & Neustadt, L.L.P.

(57) ABSTRACT

An image processing apparatus according to an embodiment includes a reception unit and a storing unit. The reception unit receives a capturing instruction to capture a stereoscopic image being displayed stereoscopically. If the reception unit receives the capturing instruction, the storing unit stores a plurality of parallax images used for displaying the stereoscopic image being displayed stereoscopically in a manner associated with one another as captured images in a predetermined storage device.

18 Claims, 7 Drawing Sheets

(56) References Cited

U.S. PATENT DOCUMENTS

| | | | |
|---|---|---|---|
| 2009/0267940 A1* | 10/2009 | Garg et al. ................... 345/419 |
| 2010/0208958 A1 | 8/2010 | Yamada et al. |
| 2011/0013890 A1 | 1/2011 | Sasaki et al. |
| 2011/0032339 A1* | 2/2011 | Hirayama et al. ............. 348/51 |
| 2011/0090309 A1 | 4/2011 | Suzuki et al. |
| 2012/0036544 A1* | 2/2012 | Chen ................... H04N 19/597 725/109 |
| 2013/0012820 A1* | 1/2013 | Brown ................... A61B 8/465 600/443 |

FOREIGN PATENT DOCUMENTS

| | | |
|---|---|---|
| JP | 10-108114 A | 4/1998 |
| JP | 2003-32702 A | 1/2003 |
| JP | 2005-86414 | 3/2005 |
| JP | 2005-349127 A | 12/2005 |
| JP | 2006-101329 A | 4/2006 |
| JP | 2006-157669 A | 6/2006 |
| JP | 2008-289064 A | 11/2008 |
| JP | 2009-59113 A | 3/2009 |
| WO | WO 2011/062572 A1 | 5/2011 |

OTHER PUBLICATIONS

Extended European Search Report issued Aug. 6, 2015 in Patent Application No. 12174909.7.
Partial European Search Report issued Apr. 2, 2015 in Patent Application No. 12174909.7.
Office Action issued Apr. 19, 2016 in Japanese Patent Application No. 2012-149239.
Office Action mailed Aug. 29, 2016 in European Application No. 12 174 909.7.

* cited by examiner

IMAGE PROCESSING APPARATUS, IMAGE PROCESSING METHOD, AND MEDICAL IMAGE DIAGNOSIS APPARATUS

CROSS-REFERENCE TO RELATED APPLICATIONS

This application is based upon and claims the benefit of priority from Japanese Patent Application No. 2011-148579, filed on Jul. 04, 2011, the entire contents of all of which are incorporated herein by reference.

FIELD

Embodiments described herein relate generally to an image processing apparatus, an image processing method, and a medical image diagnosis apparatus.

BACKGROUND

Conventionally, there has been developed a technology for displaying a stereoscopic image to a user who uses a specific device, such as a pair of stereoscopic vision glasses, by displaying two parallax images captured from two points of view on a monitor. Furthermore, in recent years, there has been developed a technology for displaying a stereoscopic image to a user without glasses by displaying multi-parallax images (e.g., nine parallax images) captured from a plurality of points of view on a monitor with a beam control element, such as a lenticular lens.

As for medical image diagnosis apparatuses, such as X-ray computed tomography (CT) apparatuses, magnetic resonance imaging (MRI) apparatuses, and ultrasound diagnosis apparatuses, there have been developed apparatuses capable of generating a three-dimensional medical image (hereinafter, referred to as volume data). Medical image diagnosis apparatuses perform various types of image processing on volume data to generate a two-dimensional image to be displayed, and display the two-dimensional image on a general-purpose monitor. Medical image diagnosis apparatuses, for example, perform volume rendering processing on volume data to generate a two-dimensional image of an arbitrary section on which three-dimensional information of a subject is reflected, and display the two-dimensional image thus generated on a general-purpose monitor.

DETAILED DESCRIPTION

According to an embodiment, an image processing apparatus includes a reception unit and a storing unit. The reception unit configured to receive a capturing instruction to capture a stereoscopic image being displayed stereoscopically. The storing unit configured to, when the reception unit receives the capturing instruction, store a plurality of parallax images used for displaying the stereoscopic image being displayed by a stereoscopic image display device in a manner associated with one another as a captured image in a predetermined storage device.

Exemplary embodiments of an image processing apparatus, an image processing method, and a medical image diagnosis apparatus are described below in greater detail with reference to the accompanying drawings. In the description below, an image processing system including a workstation having a function as an image processing apparatus will be explained as the embodiments.

First Embodiment

Figure 1:
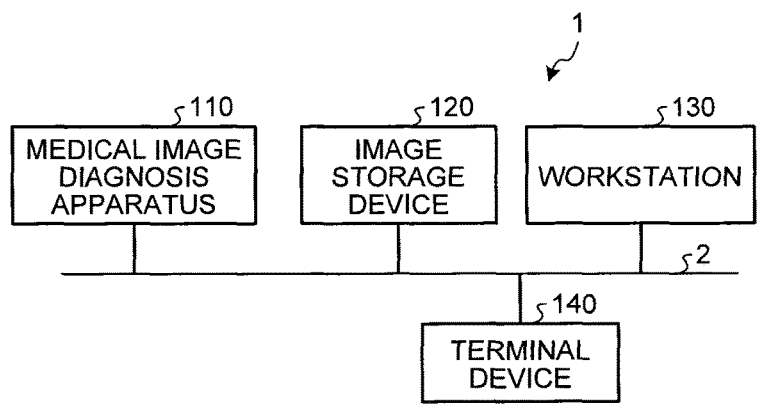
FIG. 1 is a diagram for explaining an exemplary configuration of an image processing system according to a first embodiment.

An exemplary configuration of an image processing system including an image processing apparatus according to a first embodiment will now be described. FIG. 1 is a diagram for explaining the exemplary configuration of the image processing system according to the first embodiment.

As illustrated in FIG. 1, an image processing system 1 according to the first embodiment includes a medical image diagnosis apparatus 110, an image storage device 120, a workstation 130, and a terminal device 140. The devices exemplified in FIG. 1 can communicate with one another directly or indirectly via an in-hospital local area network (LAN) 2 established in a hospital, for example. If a picture archiving and communication system (PACS) is introduced into the image processing system 1, for example, the devices transmit and receive a medical image among one another in accordance with the digital imaging and communications in medicine (DICOM) standard.

The image processing system 1 generates parallax images used for displaying a stereoscopic image based on volume data generated by the medical image diagnosis apparatus 110, and displays the parallax images thus generated on a monitor capable of displaying a stereoscopic image, thereby providing a stereoscopic image to a doctor or a laboratory technician who works for the hospital.

A "stereoscopic image" used herein is displayed to a user by displaying a plurality of parallax images captured from a plurality of points of view at different parallactic angles. In other words, "parallax images" are images captured from a plurality of points of view at different parallactic angles, and are images used for displaying a stereoscopic image to the user. Parallax images used for displaying a stereoscopic image are generated by performing volume rendering processing on volume data, for example.

A "parallax image" is an individual image constituting a "stereoscopic vision image". In other words, a "stereoscopic vision image" is composed of a plurality of "parallax images" at different "parallactic angles". A "parallax number" represents the number of "parallax images" required for achieving stereoscopic vision on a stereoscopic display monitor. A "parallactic angle" represents an angle defined by an interval between viewpoint positions set for generating a "stereoscopic vision image" and by the position of volume data. In the description below, "nine-parallax images" represent a "stereoscopic vision image" composed of nine "parallax images". Furthermore, in the description below, "two-parallax images" represent a "stereoscopic vision image" composed of two "parallax images". By displaying a stereoscopic vision image, that is, by displaying a plurality of parallax images, a "stereoscopic image" is displayed to the user.

As will be described below in detail, in the first embodiment, the workstation 130 performs various types of image processing on volume data to generate parallax images used for displaying a stereoscopic image. The workstation 130 and the terminal device 140 have a monitor capable of displaying a stereoscopic image, and display parallax images generated by the workstation 130 on the monitor, thereby displaying a stereoscopic image to the user. The image storage device 120 stores therein volume data generated by the medical image diagnosis apparatus 110 and parallax images generated by the workstation 130. The workstation 130 and the terminal device 140, for example, acquire volume data and parallax images from the image storage device 120 to perform arbitrary image processing on the volume data and the parallax images thus acquired and to display the parallax images on the monitor.

The medical image diagnosis apparatus 110 may be an X-ray diagnosis apparatus, an X-ray computed tomography (CT) apparatus, a magnetic resonance imaging (MRI) apparatus, an ultrasound diagnosis apparatus, a single photon emission computed tomography (SPECT) apparatus, a positron emission tomography (PET) apparatus, a SPECT-CT apparatus in which a SPECT apparatus and an X-ray CT apparatus are integrated, a PET-CT apparatus in which a PET apparatus and an X-ray CT apparatus are integrated, or a group of these apparatuses. The medical image diagnosis apparatus 110 generates volume data.

Specifically, the medical image diagnosis apparatus 110 according to the first embodiment captures a subject to generate volume data. The medical image diagnosis apparatus 110, for example, captures a subject to acquire data, such as projection data and an MR signal. The medical image diagnosis apparatus 110 then reconstructs medical images of a plurality of axial planes in a body axis direction of the subject based on the data thus acquired, thereby generating volume data. An explanation will be made of the case where the medical image diagnosis apparatus 110 reconstructs medical images of 500 axial planes, for example. In this case, the medical image group of 500 axial planes reconstructed by the medical image diagnosis apparatus 110 corresponds to volume data. Alternatively, the projection data and the MR signal of the subject captured by the medical image diagnosis apparatus 110 may be used as volume data, for example.

The medical image diagnosis apparatus 110 transmits volume data to the image storage device 120. When transmitting volume data to the image storage device 120, the medical image diagnosis apparatus 110 also transmits a patient ID for identifying a patient, an examination ID for identifying an examination, an apparatus ID for identifying the medical image diagnosis apparatus 110, and a series ID for identifying single capturing performed by the medical image diagnosis apparatus 110, for example.

The image storage device 120 is a database that stores therein medical images. Specifically, the image storage device 120 receives volume data from the medical image diagnosis apparatus 110, and stores the volume data thus received in a predetermined storage unit. Furthermore, the image storage device 120 receives parallax images generated form volume data by the workstation 130, and stores the parallax images thus received in a predetermined storage unit.

In the first embodiment, the volume data and the parallax images stored in the image storage device 120 are stored therein in a manner associated with a patient ID, an examination ID, an apparatus ID, a series ID, and the like. Therefore, the workstation 130 and the terminal device 140 acquire required volume data and parallax images from the image storage device 120 by performing a search with the patient ID, the examination ID, the apparatus ID, the series ID, and the like. The image storage device 120 and the workstation 130 may be integrated as a single device.

The workstation 130 is an image processing apparatus that performs image processing on a medical image. Specifically, the workstation 130 acquires volume data from the image storage device 120. The workstation 130 then performs various types of rendering processing on the volume data thus acquired to generate parallax images used for displaying a stereoscopic image. To display a two-parallax stereoscopic image to the user, for example, the workstation 130 generates two parallax images at different parallactic angles. Furthermore, to display a nine-parallax stereoscopic image to the user, for example, the workstation 130 generates nine parallax images at different parallactic angles.

The workstation 130 includes a monitor capable of displaying a stereoscopic image (also referred to as a stereoscopic display monitor or a stereoscopic image display device) as a display unit. The workstation 130 generates parallax images, and displays the parallax images thus generated on the stereoscopic display monitor, thereby displaying a stereoscopic image to the user. As a result, the user of the workstation 130 can perform an operation for generating the parallax images while checking the stereoscopic image displayed on the stereoscopic display monitor.

The workstation 130 transmits the parallax images thus generated to the image storage device 120 and the terminal device 140. When transmitting the parallax images to the image storage device 120 and the terminal device 140, the workstation 130 also transmits a patient ID, an examination ID, an apparatus ID, and a series ID, for example. At this time, based on the fact that the resolution of the monitor varies, the workstation 130 may also transmit the number of parallax images and the resolution of parallax images. The resolution may be represented by "466×350 pixels", for example.

The workstation 130 according to the first embodiment receives a capturing instruction to capture a stereoscopic image being displayed on the workstation 130 and the terminal device 140. When receiving the capturing instruction, the workstation 130 stores a plurality of parallax images used for displaying the stereoscopic image being displayed stereoscopically in a manner associated with one another as captured images in a predetermined storage device. As a result, it is possible to provide an image processing apparatus, an image processing method, and a medical image diagnosis apparatus capable of capturing a stereoscopic image.

Referring back to FIG. 1, the terminal device 140 is a terminal that allows a doctor or a laboratory technician who works for the hospital to browse a medical image. Specifically, the terminal device 140 includes a stereoscopic display monitor as a display unit. The terminal device 140 acquires parallax images from the image storage device 120, and displays the parallax images thus acquired on the stereoscopic display monitor, thereby displaying a stereoscopic image to the user. Furthermore, when receiving parallax images from the workstation 130, for example, the terminal device 140 displays the parallax images thus received on the stereoscopic display monitor, thereby displaying a stereoscopic image to the user. As a result, a doctor or a laboratory technician who is the user can browse a medical image capable of being viewed stereoscopically. The terminal device 140 may be a general-purpose personal computer (PC), a tablet terminal, or a mobile phone including the stereoscopic display monitor, for example. Alternatively, the terminal device 140 may be an arbitrary information processing terminal connected to the stereoscopic display monitor serving as an external device, for example.

The stereoscopic display monitor included in the workstation 130 and the terminal device 140 will now be described. Examples of the stereoscopic display monitor include a monitor that displays a two-parallax stereoscopic image (binocular parallax images) to the user who wears a specific device, such as a pair of stereoscopic vision glasses, by displaying two parallax images.

Figure 2A:
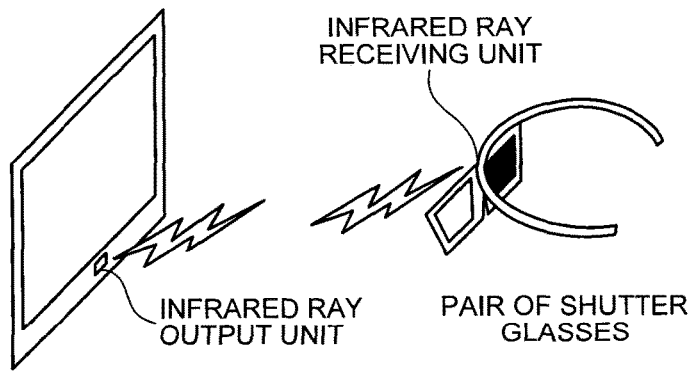
FIG. 2A and FIG. 2B are schematics for explaining an example of a stereoscopic display monitor that performs stereoscopic display using two-parallax images.
Figure 2B:
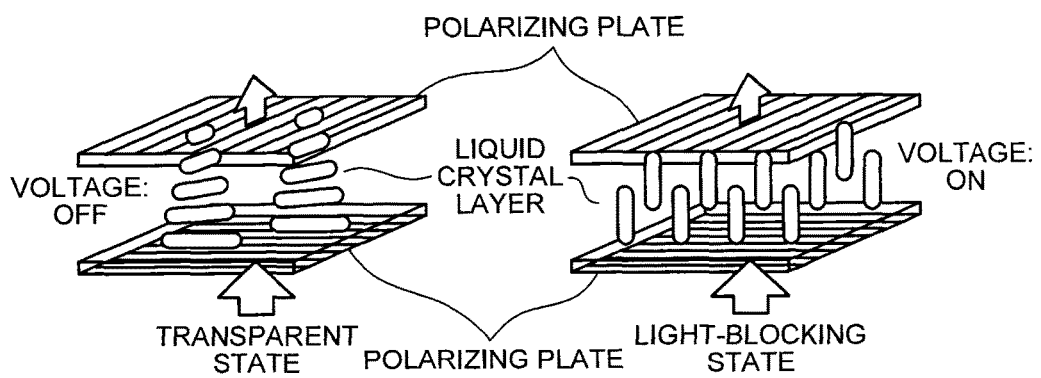

FIG. 2A and FIG. 2B are schematics for explaining an example of a stereoscopic display monitor that performs stereoscopic display using two-parallax images. The example illustrated in FIG. 2A and FIG. 2B is a stereoscopic display monitor that performs stereoscopic display by a shutter method. In the example illustrated in FIG. 2A and FIG. 2B, the user who observes the monitor wears a pair of shutter glasses as the pair of stereoscopic vision glasses. In the example illustrated in FIG. 2A and FIG. 2B, the stereoscopic display monitor outputs two parallax images alternately. The stereoscopic display monitor illustrated in FIG. 2A, for example, outputs a parallax image for the left eye and a parallax image for the right eye alternately at 120 Hz. Furthermore, as illustrated in FIG. 2A, the stereoscopic display monitor is provided with an infrared ray output unit. The infrared ray output unit controls output of infrared rays in synchronization with an operational timing at which the parallax images are switched.

Furthermore, as illustrated in FIG. 2A, an infrared ray receiving unit of the pair of shutter glasses receives the infrared rays output from the infrared ray output unit. A shutter is attached to a left frame and a right frame of the pair of shutter glasses. The pair of shutter glasses switches the state of the left shutter and the right shutter between a transparent state and a light-blocking state alternately in synchronization with an operational timing at which the infrared ray receiving unit receives the infrared rays.

The switching processing for the shutters of the pair of shutter glasses between the transparent state and the light-blocking state will now be described. As illustrated in FIG. 2B, each of the shutters includes an incident-side polarizing plate, an output-side polarizing plate, and a liquid crystal layer between the incident-side polarizing plate and the output-side polarizing plate. As illustrated in FIG. 2B, the incident-side polarizing plate and the output-side polarizing plate are arranged in a manner orthogonal to each other. As illustrated in FIG. 2B, in an "OFF" state where no voltage is applied, light passing through the incident-side polarizing plate is caused to rotate 90 degrees by an action of the liquid crystal layer to pass through the output-side polarizing plate. In other words, a shutter to which no voltage is applied is in the transparent state.

By contrast, as illustrated in FIG. 2B, in an "ON" state where a voltage is applied, a polarization rotation effect caused by liquid crystal molecules of the liquid crystal layer vanishes, whereby light passing through the incident-side polarizing plate is blocked by the output-side polarizing plate. In other words, a shutter to which a voltage is applied is in the light-blocking state.

Based on this, the infrared ray output unit of the stereoscopic display monitor outputs infrared rays while the image for the left eye is being displayed on the monitor, for example. The infrared ray receiving unit of the pair of shutter glasses applies no voltage to the left-eye shutter, and applies a voltage to the right-eye shutter while receiving the infrared rays. Thus, as illustrated in FIG. 2A, the right-eye shutter is in the light-blocking state, and the left-eye shutter is in the transparent state, whereby the image for the left eye is incident only on the left eye of the user. By contrast, the infrared ray output unit of the stereoscopic display monitor stops output of the infrared rays while the image for the right eye is being displayed on the monitor, for example. The infrared ray receiving unit of the pair of shutter glasses applies no voltage to the right-eye shutter, and applies a voltage to the left-eye shutter while receiving no infrared ray. Thus, the left-eye shutter is in the light-blocking state, and the right-eye shutter is in the transparent state, whereby the image for the right eye is incident only on the right eye of the user. As described above, the stereoscopic display monitor illustrated in FIG. 2A and FIG. 2B switches the images displayed on the monitor in synchronization with the state of the shutters, thereby displaying a stereoscopic image to the user.

Furthermore, examples of the stereoscopic display monitor include a monitor that displays a nine-parallax stereoscopic image to the user without glasses by using a beam control element, such as a lenticular lens. In this case, the stereoscopic display monitor enables stereoscopic vision by binocular parallax. Furthermore, the stereoscopic display monitor can display a stereoscopic image having motion parallax in which video to be observed by the user changes in synchronization with movement of the viewpoint of the user.

Figure 3:
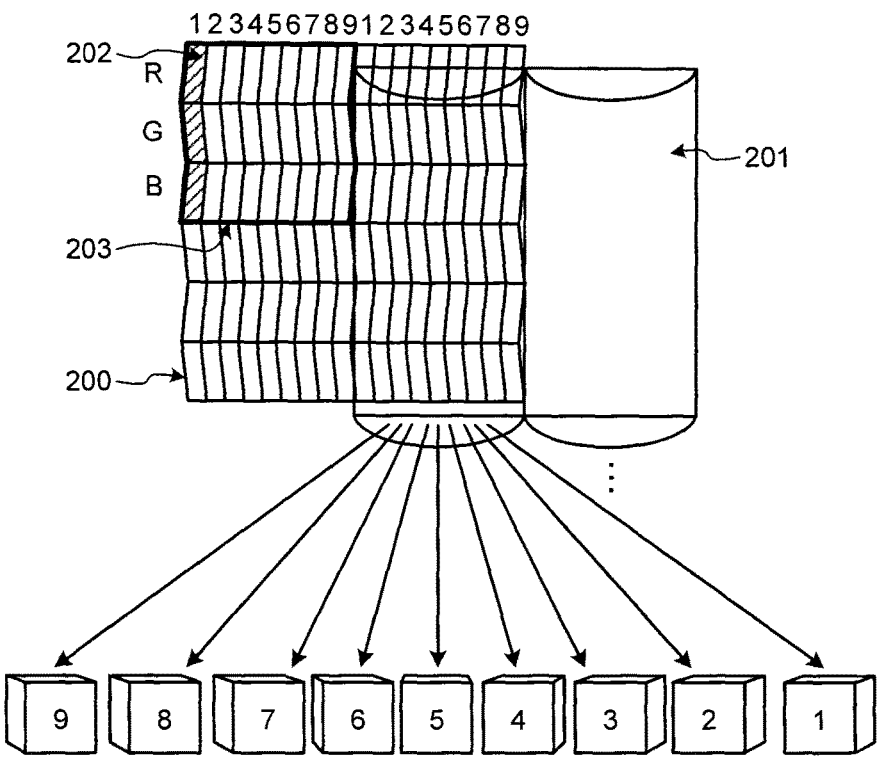
FIG. 3 is a schematic for explaining an example of a stereoscopic display monitor that performs stereoscopic display using nine-parallax images.

FIG. 3 is a schematic for explaining an example of a stereoscopic display monitor that performs stereoscopic display using nine-parallax images. In the stereoscopic display monitor illustrated in FIG. 3, a beam control element is arranged in front of a display surface 200 in a planar shape, such as a liquid crystal panel. In the stereoscopic display monitor illustrated in FIG. 3, for example, a vertical lenticular sheet 201 whose optical aperture extends in the vertical direction is attached to the front of the display surface 200 as the beam control element. In the example illustrated in FIG. 3, the vertical lenticular sheet 201 is attached such that a convex portion thereof faces the front. Alternatively, the vertical lenticular sheet 201 may be attached such that the convex portion thereof faces the display surface 200.

In the example illustrated in FIG. 3, pixels 202 whose aspect ratio is 3 to 1 and in which three sub pixels of red (R), green (G), and blue (B) are aligned in the longitudinal direction are arranged in a matrix manner on the display surface 200. In the example illustrated in FIG. 3, the stereoscopic display monitor arranges nine parallax images at different parallactic angles in a predetermined format (e.g., a grid pattern), and outputs the nine parallax images to the display surface 200. In other words, the stereoscopic display monitor illustrated in FIG. 3 displays an intermediate image in which nine pixels at the same position in the nine parallax images at different parallactic angles are allocated to the pixels 202 of nine columns. The pixels 202 of nine columns are a unit pixel group 203 that displays nine images at different parallactic angles simultaneously. In the example illustrated in FIG. 3, the intermediate image is in a grid pattern. However, it is not limited thereto, and the intermediate image may be in an arbitrary format.

The nine parallax images at different parallactic angles output simultaneously as the unit pixel group 203 on the display surface 200 are emitted as parallel light by a light emitting diode (LED) back light, for example, and are emitted in multi-directions by the vertical lenticular sheet 201. Light of each pixel in the nine parallax images is emitted in multi-directions, whereby light incident on the right eye and the left eye of the user changes in synchronization with the position of the user (position of the viewpoint). In other words, the parallax image incident on the right eye and the parallax image incident on the left eye have different parallactic angles depending on the viewing angle of the user. As a result, the user can view a stereoscopic image in a manner viewing a captured subject from different parallactic angles at each of the nine positions illustrated in FIG. 3, for example. Furthermore, the user can view the captured subject stereoscopically in a manner facing the captured subject at the position of "5" illustrated in FIG. 3, and can view the captured subject stereoscopically such that the orientation of the captured subject is changed at each of the positions other than "5" illustrated in FIG. 3, for example. The example illustrated in FIG. 3 is given just as an example, and the stereoscopic display monitor is not limited thereto. In the example illustrated in FIG. 3, explanation has been made of a combination of a horizontal stripe (RRR . . . , GGG . . . , BBB . . . ) liquid crystal and a vertical lens. However, the stereoscopic display monitor is not limited thereto, and a combination of a vertical stripe (RGBRGB . . . ) liquid crystal and an oblique lens may be employed, for example.

The exemplary configuration of the image processing system 1 according to the first embodiment has been explained briefly. Application of the image processing system 1 is not limited to the case where the PACS is introduced. The image processing system 1 may also be applied to the case where an electronic chart system is introduced for managing electronic charts to which medical images are attached, for example. In this case, the image storage device 120 corresponds to a database that stores therein the electronic charts. Furthermore, the image processing system 1 may also be applied to the case where a hospital information system (HIS) or a radiology information system (RIS) is introduced, for example. The configuration of the image processing system 1 is not limited to the exemplary configuration described above. Functions of each device and assignation thereof may be changed as appropriate depending on aspects of operations.

Figure 4:
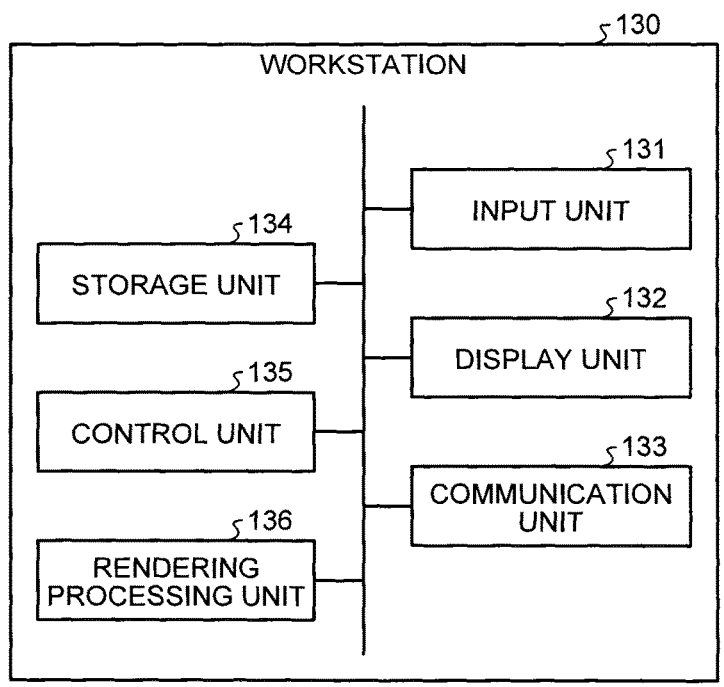
FIG. 4 is a diagram for explaining an exemplary configuration of a workstation according to the first embodiment.

An exemplary configuration of the workstation 130 according to the first embodiment will now be described with reference to FIG. 4. FIG. 4 is a diagram for explaining the exemplary configuration of the workstation according to the first embodiment.

The workstation 130 is a sophisticated computer suitable for image processing, for example. In the example illustrated in FIG. 4, the workstation 130 includes an input unit 131, a display unit 132, a communication unit 133, a storage unit 134, a control unit 135, and a rendering processing unit 136. An explanation will be made of the case where the workstation 130 is a sophisticated computer suitable for image processing, for example. However, the workstation 130 is not limited thereto, and may be an arbitrary information processing apparatus. The workstation 130 may be an arbitrary personal computer, for example.

The input unit 131 is a mouse, a keyboard, and a trackball, for example, and receives input of various types of operations to the workstation 130 from the user. Specifically, the input unit 131 receives input of information used for acquiring volume data to be a target of rendering processing from the image storage device 120. The input unit 131 receives input of a patient ID, an examination ID, an apparatus ID, and a series ID, for example. Furthermore, the input unit 131 receives input of conditions related to rendering processing (hereinafter, referred to as rendering conditions).

Furthermore, the input unit 131 receives input of setting conditions for displaying an annotation, such as a figure, an arrow, a symbol, and a character, on three-dimensional information of the subject indicated by volume data and of an instruction to display the annotation.

The input unit 131, for example, receives setting conditions for displaying an arrow indicating arbitrary coordinates in the three-dimensional information of the subject. More specifically, the input unit 131 receives setting of coordinates serving as a start point of the arrow and setting of coordinates serving as an end point of the arrow, for example. Furthermore, the input unit 131, for example, receives setting conditions for displaying an arbitrary character string on arbitrary coordinates in the three-dimensional information of the subject. More specifically, the input unit 131 receives setting of coordinates on which the arbitrary character string is to be displayed and setting of the character string to be displayed, for example. The coordinates are set with the mouse, for example. The character string is set with the keyboard, for example.

The display unit 132 is a liquid crystal panel serving as the stereoscopic display monitor, for example, and displays various types of information. Specifically, the display unit 132 according to the first embodiment displays a graphical user interface (GUI) for receiving various types of operations from the user and a stereoscopic image, for example. The communication unit 133 is a network interface card (NIC), for example, and performs communications with other devices. The communication unit 133, for example, receives rendering conditions input to the terminal device 140 by the user from the terminal device 140.

The storage unit 134 is a hard disc or a semiconductor memory element, for example, and stores therein various types of information. Specifically, the storage unit 134 stores therein volume data acquired from the image storage device 120 via the communication unit 133. Furthermore, the storage unit 134 stores therein volume data being subjected to rendering processing, parallax images already subjected to the rendering processing, and the parallax number and the resolution of the parallax images, for example.

The control unit 135 is an electronic circuit, such as a central processing unit (CPU), a micro processing unit (MPU), and a graphics processing unit (GPU), or an integrated circuit, such as an application specific integrated circuit (ASIC) and a field programmable gate array (FPGA), and controls the workstation 130 collectively.

The control unit 135, for example, controls display of the GUI and display of a stereoscopic image on the display unit 132. The control unit 135, for example, controls transmission and reception of volume data and parallax images to and from the image storage device 120 via the communication unit 133. The control unit 135, for example, controls rendering processing performed by the rendering processing unit 136. The control unit 135, for example, controls reading of volume data from the storage unit 134 and storing of parallax images in the storage unit 134.

If the input unit 131 receives setting conditions for displaying an annotation, for example, the control unit 135 stores the setting conditions received by the input unit 131 as additional information for volume data of the subject on which the annotation is set. The control unit 135, for example, outputs the setting conditions received by the input unit 131 to the image storage device 120 as the additional information, thereby causing the image storage device 120 to store therein the setting conditions as the additional information of the volume data. In other words, in this case, the image storage device 120 stores therein the volume data on which the setting conditions for displaying the annotation are set as the additional information.

The explanation has been made of the case where the input unit 131 receives setting conditions and the control unit 135 stores the setting conditions received by the input unit 131 as additional information. However, it is not limited thereto. Alternatively, for example, if the input unit 131 receives an instruction to display an annotation, the control unit 135 may generate setting conditions for displaying the annotation specified by the instruction received by the input unit 131, and store the setting conditions thus generated as additional information. An explanation will be made of the case where the input unit 131 receives an instruction to display a scale indicating the depth together with the three-dimensional information of the subject. In this case, the control unit 135 determines arbitrary coordinates on which the scale is to be displayed in the three-dimensional information of the subject. Subsequently, the control unit 135 generates setting conditions for displaying the scale indicating the depth on the coordinates thus determined, and stores the setting conditions thus generated as additional information.

The control unit 135 of the workstation 130 controls rendering processing performed by the rendering processing unit 136, and cooperates with the rendering processing unit 136 to perform measurement processing. The control unit 135 will be described in detail after the description of the rendering processing unit 136.

The rendering processing unit 136 performs various types of rendering processing on volume data acquired from the image storage device 120 under the control of the control unit 135 to generate parallax images. Specifically, the rendering processing unit 136 reads volume data from the storage unit 134, and performs preprocessing on the volume data thus read. The rendering processing unit 136 then performs volume rendering processing on the volume data subjected to the preprocessing to generate parallax images used for displaying a stereoscopic image. Subsequently, the rendering processing unit 136 stores the parallax images thus generated in the storage unit 134.

Furthermore, the rendering processing unit 136 may generate an overlay image on which various types of information (e.g., a scale, a patient's name, and an examination item) are depicted, and superimpose the overlay image thus generated on the parallax images. In this case, the rendering processing unit 136 stores the parallax images on which the overlay image is superimposed in the storage unit 134.

If the input unit 131 receives setting conditions for displaying an annotation, for example, the rendering processing unit 136 generates an overlay image for displaying the annotation thus received. The rendering processing unit 136, for example, generates an overlay image for displaying an arrow indicating arbitrary coordinates and sets an overlay image for displaying an arbitrary character string on arbitrary coordinates in the three-dimensional information of the subject.

More specifically, the rendering processing unit 136 generates an overlay image for displaying an annotation based on setting conditions received by the input unit 131 or additional information of volume data.

An additional explanation will be made of the relationship among the annotation, the additional information, and the overlay image. As described above, the annotation is a figure, a symbol, a character string, or an arrow, for example. The additional information is setting information for displaying the annotation, and is coordinates of the start point and the end point of the arrow, coordinates on which an arbitrary character string is to be displayed, or the character string to be displayed as the annotation, for example. The overlay image is an image displayed in a manner superimposed on parallax images, and corresponds to an image for displaying the annotation. The overlay image is generated based on the setting information for displaying the annotation and the additional information.

The rendering processing represents the entire image processing performed on volume data. The volume rendering processing represents processing for generating a medical image on which the three-dimensional information of the subject is reflected in the rendering processing. The medical image generated by the rendering processing corresponds to a parallax image, for example.

Figure 5:
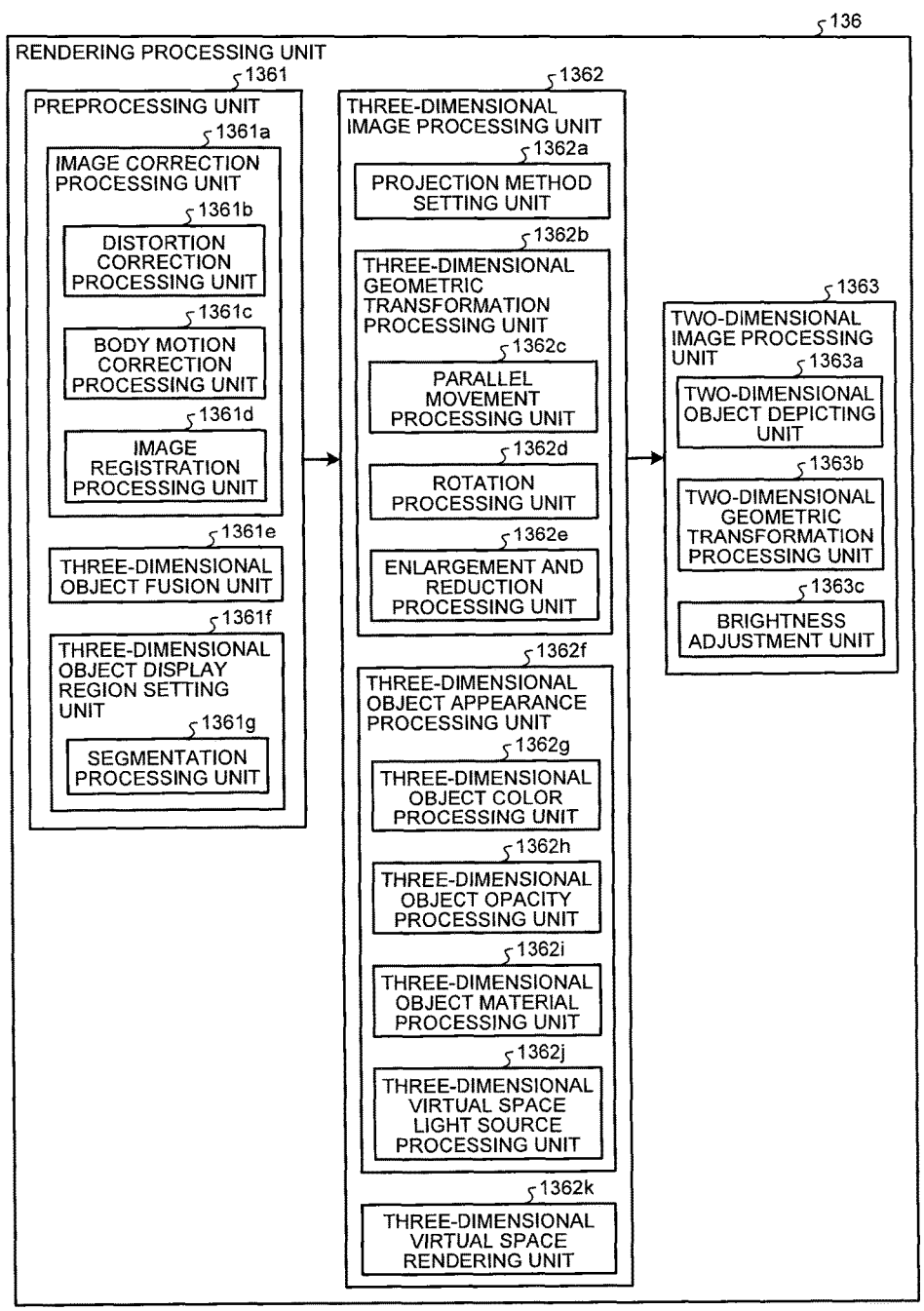
FIG. 5 is a diagram for explaining an exemplary configuration of a rendering processing unit illustrated in FIG. 4.

FIG. 5 is a diagram for explaining an exemplary configuration of the rendering processing unit illustrated in FIG. 4. As illustrated in FIG. 5, the rendering processing unit 136 includes a preprocessing unit 1361, a three-dimensional image processing unit 1362, and a two-dimensional image processing unit 1363. As will be described below in detail, the preprocessing unit 1361 performs preprocessing on volume data. The three-dimensional image processing unit 1362 generates parallax images from the volume data subjected to the preprocessing. The two-dimensional image processing unit 1363 generates parallax images obtained by superimposing various types of information on a stereoscopic image.

The preprocessing unit 1361 performs various types of preprocessing when rendering processing is performed on volume data. In the example illustrated in FIG. 5, the preprocessing unit 1361 includes an image correction processing unit 1361a, a three-dimensional object fusion unit 1361e, and a three-dimensional object display region setting unit 1361f.

The image correction processing unit 1361a performs image correction processing when two types of volume data are processed as one piece of volume data. In the example illustrated in FIG. 5, the image correction processing unit 1361a includes a distortion correction processing unit 1361b, a body motion correction processing unit 1361c, and an image registration processing unit 1361d. The image correction processing unit 1361a, for example, performs image correction processing when volume data of a PET image and volume data of an X-ray CT image generated by a PET-CT apparatus are processed as one piece of volume data. Furthermore, the image correction processing unit 1361a performs image correction processing when volume data of a T1-weighted image and volume data of a T2-weighted image generated by an MRI apparatus are processed as one piece of volume data.

The distortion correction processing unit 1361b of the image correction processing unit 1361a corrects distortion of data in individual volume data caused by acquisition conditions in data acquisition performed by the medical image diagnosis apparatus 110. The body motion correction processing unit 1361c corrects movement caused by body motion of the subject during an acquisition time of data used for generating individual volume data. The image registration processing unit 1361d performs registration using a cross-correlation method, for example, between two pieces of volume data on which the correction processing is performed by the distortion correction processing unit 1361b and the body motion correction processing unit 1361c.

The three-dimensional object fusion unit 1361e fuses a plurality of pieces of volume data on which registration is performed by the image registration processing unit 1361d. The processing performed by the image correction processing unit 1361a and the three-dimensional object fusion unit 1361e is omitted if rendering processing is performed on a single piece of volume data.

The three-dimensional object display region setting unit 1361f sets a display region corresponding to an organ to be displayed that is specified by the user. In the example illustrated in FIG. 5, the three-dimensional object display region setting unit 1361f includes a segmentation processing unit 1361g. The segmentation processing unit 1361g of the three-dimensional object display region setting unit 1361f extracts an organ, such as a heart, a lung, and a blood vessel, specified by the user with a region growing method based on the pixel value of volume data (voxel value), for example.

If the user specifies no organ to be displayed, the segmentation processing unit 1361g performs no segmentation processing. By contrast, if the user specifies a plurality of organs to be displayed, the segmentation processing unit 1361g extracts a plurality of organs corresponding thereto. The processing of the segmentation processing unit 1361g may be performed again in response to a request for fine adjustment from the user who refers to a rendering image.

The three-dimensional image processing unit 1362 performs volume rendering processing on the volume data on which the preprocessing is performed by the preprocessing unit 1361. In the example illustrated in FIG. 5, the three-dimensional image processing unit 1362 serves as a processing unit that performs volume rendering processing, and includes a projection method setting unit 1362a, a three-dimensional geometric transformation processing unit 1362b, a three-dimensional object appearance processing unit 1362f, and a three-dimensional virtual space rendering unit 1362k.

The projection method setting unit 1362a determines a projection method for generating a stereoscopic image. The projection method setting unit 1362a, for example, determines whether to perform the volume rendering processing by a parallel projection method or a perspective projection method.

The three-dimensional geometric transformation processing unit 1362b determines information used for three-dimensionally geometrically transforming volume data on which the volume rendering processing is to be performed. In the example illustrated in FIG. 5, the three-dimensional geometric transformation processing unit 1362b includes a parallel movement processing unit 1362c, a rotation processing unit 1362d, and an enlargement and reduction processing unit 1362e. The parallel movement processing unit 1362c of the three-dimensional geometric transformation processing unit 1362b determines a movement amount by which the volume data is moved in a parallel manner if the viewpoint position is moved in a parallel manner while the volume rendering processing is being performed. The rotation processing unit 1362d determines a movement amount by which the volume data is moved rotationally if the viewpoint position is moved rotationally while the volume rendering processing is being performed. The enlargement and reduction processing unit 1362e determines an enlargement ratio or a reduction ratio of the volume data if enlargement or reduction of a stereoscopic image is requested.

The three-dimensional object appearance processing unit 1362f includes a three-dimensional object color processing unit 1362g, a three-dimensional object opacity processing unit 1362h, a three-dimensional object material processing unit 1362i, and a three-dimensional virtual space light source processing unit 1362j. The three-dimensional object appearance processing unit 1362f determines a display state of a stereoscopic image to be displayed to the user by displaying parallax images with these processing units in response to a request from the user, for example.

The three-dimensional object color processing unit 1362g determines a color applied to each region segmented in the volume data. The three-dimensional object opacity processing unit 1362h determines the opacity of each voxel constituting each region segmented in the volume data. A region behind a region whose opacity is determined to be "100%" in the volume data is not depicted in the parallax images. Furthermore, a region whose opacity is determined to be "0%" in the volume data is not depicted in the parallax images.

The three-dimensional object material processing unit 1362i determines a material of each region segmented in the volume data to adjust texture when the region is depicted. The three-dimensional virtual space light source processing unit 1362j determines the position of a virtual light source arranged in a three-dimensional virtual space and the type of the virtual light source when the volume rendering processing is performed on the volume data. Examples of the type of the virtual light source include a light source that emits parallel light beams from infinity and a light source that emits radial light beams from the point of view.

The three-dimensional virtual space rendering unit 1362k performs volume rendering processing on volume data to generate parallax images. To perform the volume rendering processing, the three-dimensional virtual space rendering unit 1362k uses various types of information determined by the projection method setting unit 1362a, the three-dimensional geometric transformation processing unit 1362b, and the three-dimensional object appearance processing unit 1362f as needed.

The three-dimensional virtual space rendering unit 1362k receives rendering conditions from the control unit 135, and performs volume rendering processing on volume data in accordance with the rendering conditions thus received. The rendering conditions are received from the user via the input unit 131, are set by default, or are received from the terminal device 140 via the communication unit 133. At this time, the projection method setting unit 1362a, the three-dimensional geometric transformation processing unit 1362b, and the three-dimensional object appearance processing unit 1362f determine required various types of information in accordance with the rendering conditions. As a result, the three-dimensional virtual space rendering unit 1362k uses the various types of information thus determined to generate a stereoscopic image.

Examples of the rendering conditions include "the parallel projection method" and "the perspective projection method". Examples of the rendering conditions also include "a reference viewpoint position and a parallactic angle". Examples of the rendering conditions also include "parallel movement of the viewpoint position", "rotational movement of the viewpoint position", "enlargement of the stereoscopic image", and "reduction of the stereoscopic image".

Examples of the rendering conditions also include "a color to be applied", "transmittance", "texture", "the position of the virtual light source", and "the type of the virtual light source".

Figure 6:
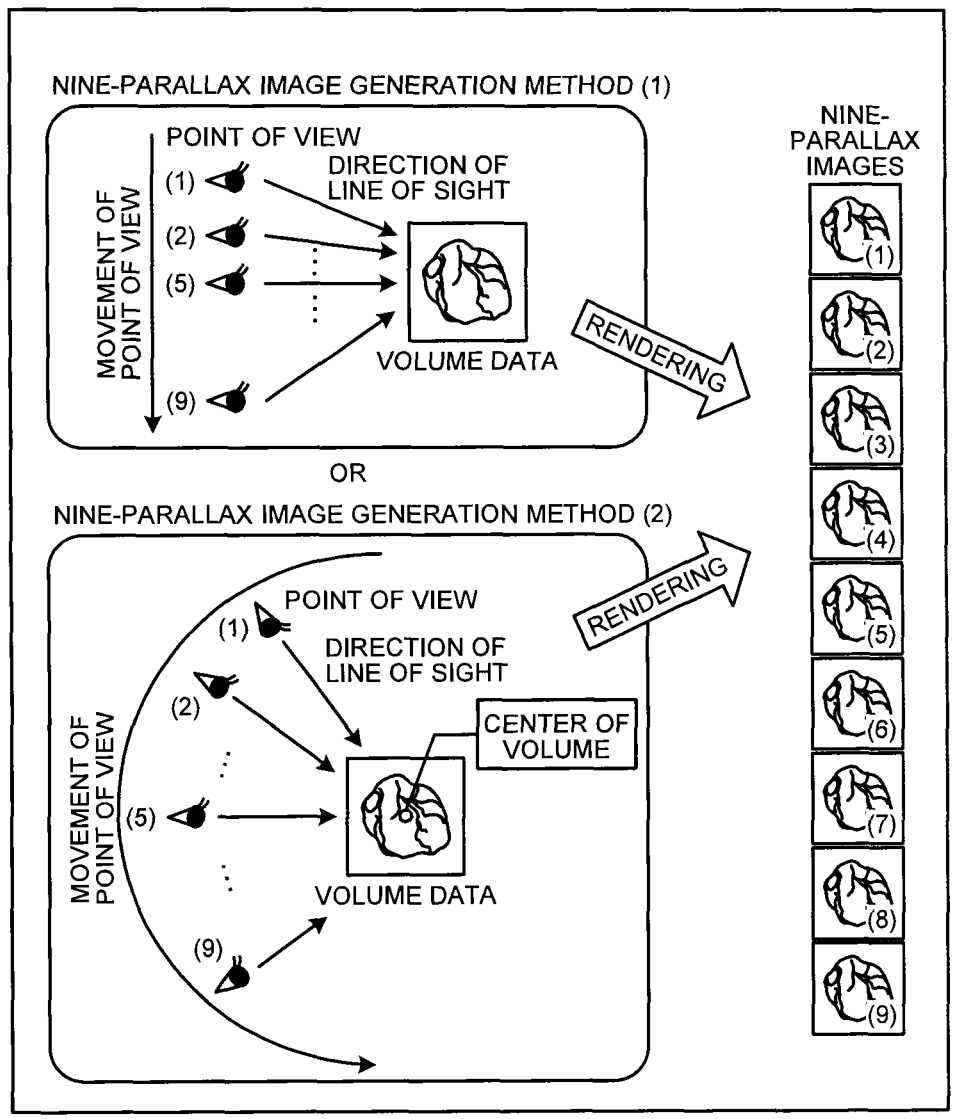
FIG. 6 is a schematic for explaining an example of volume rendering processing according to the first embodiment.

FIG. 6 is a schematic for explaining an example of the volume rendering processing according to the first embodiment. As illustrated in a "nine-parallax image generation method (1)" in FIG. 6, for example, an assumption is made that the three-dimensional virtual space rendering unit 1362k receives the parallel projection method, a reference viewpoint position (5), and a parallactic angle of "1 degree" as the rendering conditions. In this case, the three-dimensional virtual space rendering unit 1362k moves the position of the viewpoint from (1) to (9) in a parallel manner by a parallactic angle of "1 degree". Thus, the three-dimensional virtual space rendering unit 1362k generates nine parallax images whose parallactic angles are set to 1 degree by the parallel projection method. To employ the parallel projection method, the three-dimensional virtual space rendering unit 1362k sets a light source that emits parallel light beams from infinity along a direction of a line of sight.

Alternatively, as illustrated in a "nine-parallax image generation method (2)" in FIG. 6, an assumption is made that the three-dimensional virtual space rendering unit 1362k receives the perspective projection method, a reference viewpoint position (5), and a parallactic angle of "1 degree" as the rendering conditions. In this case, the three-dimensional virtual space rendering unit 1362k moves the position of the viewpoint from (1) to (9) rotationally by a parallactic angle of "1 degree" about the center of gravity of a section of the volume data that is present on a plane along which the viewpoint is moved. Thus, the three-dimensional virtual space rendering unit 1362k generates nine parallax images whose parallactic angles are set to 1 degree by the perspective projection method. In other words, the three-dimensional virtual space rendering unit 1362k generates the nine parallax images by moving the viewpoint position rotationally not about the center of gravity of the three-dimensional volume, but about the center of gravity of the two-dimensional section. To employ the perspective projection method, the three-dimensional virtual space rendering unit 1362k sets a point light source or a surface light source that emits light in a three-dimensionally radial manner about the direction of the line of sight for each viewpoint. Furthermore, to employ the perspective projection method, the viewpoints (1) to (9) may be realized by parallel movement depending on the rendering conditions.

The three-dimensional virtual space rendering unit 1362k may set a light source that emits light in a two-dimensionally radial manner about the direction of the line of sight with respect to the vertical direction of the volume rendering image to be displayed and that emits parallel light beams from infinity along the direction of the line of sight with respect to the horizontal direction of the volume rendering image to be displayed. Thus, the three-dimensional virtual space rendering unit 1362k may perform volume rendering processing by combining the parallel projection method and the perspective projection method.

In the example illustrated in FIG. 6, the explanation has been made of the case where the projection method, the reference viewpoint position, and the parallactic angle are received as the rendering conditions. However, if other conditions are received as the rendering conditions, the three-dimensional virtual space rendering unit 1362k also generates nine parallax images while reflecting each rendering condition.

The three-dimensional virtual space rendering unit 1362k also has a function to reconstruct a multi planer reconstruction (MPR) image from volume data by performing MPR besides volume rendering. Furthermore, the three-dimensional virtual space rendering unit 1362k also has a function to perform "curved MPR" as the MPR and a function to perform "intensity projection".

A parallax image generated from the volume data by the three-dimensional image processing unit 1362 may be used as an underlay, and an overlay image on which various types of information (e.g., a scale, a patient's name, and an examination item) are depicted may be superimposed on the parallax image as an overlay. In this case, the two-dimensional image processing unit 1363 performs image processing on the overlay image serving as the overlay and the parallax image serving as the underlay, thereby generating a parallax image on which the overlay image is superimposed. In the example illustrated in FIG. 5, the two-dimensional image processing unit 1363 includes a two-dimensional object depicting unit 1363a, a two-dimensional geometric transformation processing unit 1363b, and a brightness adjustment unit 1363c. To reduce costs for depiction processing of the various types of information, the two-dimensional image processing unit 1363 may depict only a single overlay, and superimpose the single overlay on each of the nine parallax images serving as the underlays, thereby generating nine parallax images on which the overlay image is superimposed.

The two-dimensional object depicting unit 1363a depicts various types of information to be depicted on the overlay. The two-dimensional geometric transformation processing unit 1363b performs parallel movement processing or rotational movement processing on the positions of the various types of information depicted on the overlay, and performs enlargement processing or reduction processing on the various types of information depicted on the overlay. The brightness adjustment unit 1363c adjusts the brightness of the overlay and the underlay depending on parameters for image processing, such as gradation of the stereoscopic display monitor to which the parallax images are output, the window width (WW), and the window level (WL), for example.

The parallax images generated by the rendering processing unit 136 are temporarily stored in the storage unit 134 by the control unit 135, for example, and are transmitted to the image storage device 120 via the communication unit 133. Subsequently, the terminal device 140, for example, acquires the parallax images on which the overlay image is superimposed from the image storage device 120, converts the parallax images into an intermediate image arranged in a predetermined format (e.g., a grid pattern), and displays the intermediate image on the stereoscopic display monitor. Thus, the terminal device 140 can display a stereoscopic image with the various types of information (e.g., a scale, a patient's name, and an examination item) depicted thereon to a doctor or a laboratory technician who is the user.

As described above, the rendering processing unit 136 generates parallax images from volume data under the control of the control unit 135. The control unit 135 according to the first embodiment will now be described in detail.

Figure 7:
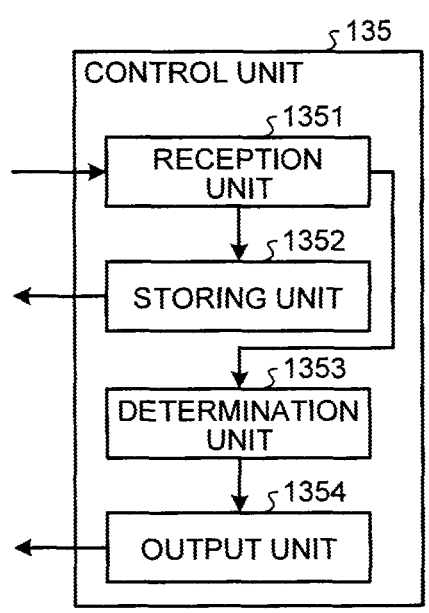
FIG. 7 is a diagram for explaining a control unit according to the first embodiment in detail.

FIG. 7 is a diagram for explaining the control unit according to the first embodiment in detail. As illustrated in FIG. 7, the control unit 135 includes a reception unit 1351, a storing unit 1352, a determination unit 1353, and an output unit 1354.

The reception unit 1351 receives a capturing instruction to capture a stereoscopic image being displayed on the workstation 130 and the terminal device 140. The reception unit 1351, for example, receives a capturing instruction while a stereoscopic image is being displayed on the workstation 130 and the terminal device 140. Furthermore, the reception unit 1351 receives an output instruction to output a captured image stored in response to the capturing instruction. The capturing instruction and the output instruction are input by the user who uses the workstation 130 and the terminal device 140.

If the reception unit 1351 receives the capturing instruction, the storing unit 1352 stores a plurality of parallax images used for displaying the stereoscopic image being displayed on the workstation 130 and the terminal device 140 in a manner associated with one another as captured images in a predetermined storage device. The storing unit 1352, for example, stores the captured images in the image storage device 120, or stores the captured images in the storage unit 134.

The captured image stored by the storing unit 1352 will now be further described. An explanation will be made of the case where the workstation 130 and the terminal device 140 display a stereoscopic image to the user by displaying two parallax images, for example. In this case, the storing unit 1352 stores the two parallax images in a manner associated with each other as captured images. Furthermore, an explanation will be made of the case where the workstation 130 and the terminal device 140 display a nine-parallax stereoscopic image to the user by displaying an intermediate image in which nine pixels at the same position in nine parallax images are allocated to the pixels 202 of nine columns, for example. In this case, the storing unit 1352 stores the nine parallax images in a manner associated with one another as captured images. In other words, the storing unit 1352 stores all the parallax images used for displaying the stereoscopic image being displayed by the workstation 130 and the terminal device 140 in a manner associated with one another.

An explanation will be made of the case where overlay images for displaying an annotation are superimposed on the parallax images displayed by the workstation 130 and the terminal device 140. In other words, an explanation will be made of the case where the stereoscopic image being displayed stereoscopically by the workstation 130 and the terminal device 140 is displayed by displaying the parallax images on which overlay images for displaying an annotation are superimposed.

In this case, for example, the storing unit 1352 integrates each overlay image superimposed on each of the parallax images with each of the parallax images, and stores each of the parallax images integrated with each of the overlay images as a captured image. In other words, the storing unit 1352 embeds the annotation, such as a character and a figure, displayed as the overlay image in the parallax images, and stores each of the parallax images in which the annotation, such as a character and a figure, is embedded as a captured image.

The storing unit 1352, for example, stores each of the parallax images and each of the overlay images superimposed on each of the parallax images in a manner associated with each other as a captured image. In other words, the storing unit 1352 associates each of the parallax images with each of the overlay images, and stores each of the parallax images and each of the overlay images in a splittable manner as a captured image.

The storing unit 1352, for example, acquires additional information of the volume data used for generating each of the parallax images for displaying the stereoscopic image being displayed stereoscopically, and stores the additional information thus acquired and each of the parallax images in a manner associated with each other as a captured image.

Whether to store each of the parallax images integrated with each of the overlay images as a captured image, whether to store each of the parallax images and each of the overlay images in a manner associated with each other as a captured image, or whether to store each of the parallax images and the additional information in a manner associated with each other as a captured image may be determined by the user when issuing the capturing instruction, or may be determined by an arbitrary method, for example.

The determination unit 1353 determines the parallax number of an image to be displayed by a display device serving as a destination of the captured image. If the reception unit 1351 receives an output instruction, for example, the determination unit 1353 determines the parallax number capable of being displayed by a device to which the user inputs the output instruction. More specifically, the determination unit 1353 determines that the parallax number is nine, two, or one, for example. The determination unit 1353 determines that the parallax number is one when the device is a display device that displays no stereoscopic image. The display device serving as the destination of the captured image is the workstation 130 or the terminal device 140, for example.

The display device serving as the destination of the captured image will now be further described. The destination of the captured image is specified by the output instruction or specified in advance by the user, for example.

While an explanation will be made of the case where the determination unit 1353 determines the parallax number if the reception unit 1351 receives an output instruction, it is not limited thereto. The determination unit 1353 may determine the parallax number in advance for a destination to which the captured image is likely to be output, for example.

The output unit 1354 outputs parallax images of the parallax number determined by the determination unit 1353 as captured images among a plurality of parallax images stored by the storing unit 1352 as the captured images. In other words, the output unit 1354 outputs parallax images of the parallax number to be displayed by the display device serving as the destination of the captured images specified by the output instruction.

A further explanation will be made of the case where the captured image to be output is each of the parallax images associated with each of the overlay images. In this case, parallax images of the parallax number determined by the determination unit 1353 are each selected and output together with each of the overlay images associated with each of the parallax images thus selected. However, it is not limited thereto, and the output unit 1354 may superimpose each of the overlay images on each of the parallax images to output each of the parallax images on which each of the overlay images is superimposed, for example. Furthermore, for example, the output unit 1354 may not superimpose each of the overlay images. By outputting each of the parallax images with no overlay image superimposed thereon in a manner associated with each of the overlay images, the output unit 1354 may output the captured image such that the user can edit the overlay images. The output unit 1354, for example, may output the parallax images with no overlay image superimposed thereon alone.

An explanation will be made of the case where the captured image to be output is each of the parallax images associated with additional information. In this case, the output unit 1354 selects parallax images of the parallax number determined by the determination unit 1353, and generates overlay images for the parallax images thus selected based on the additional information. The output unit 1354 then superimposes each of the overlay images thus generated on each of the parallax images thus selected, and outputs the parallax images. However, it is not limited thereto, and the output unit 1354 may output the parallax images thus selected without any change, or may output the parallax images and the additional information itself, for example.

Figure 8:
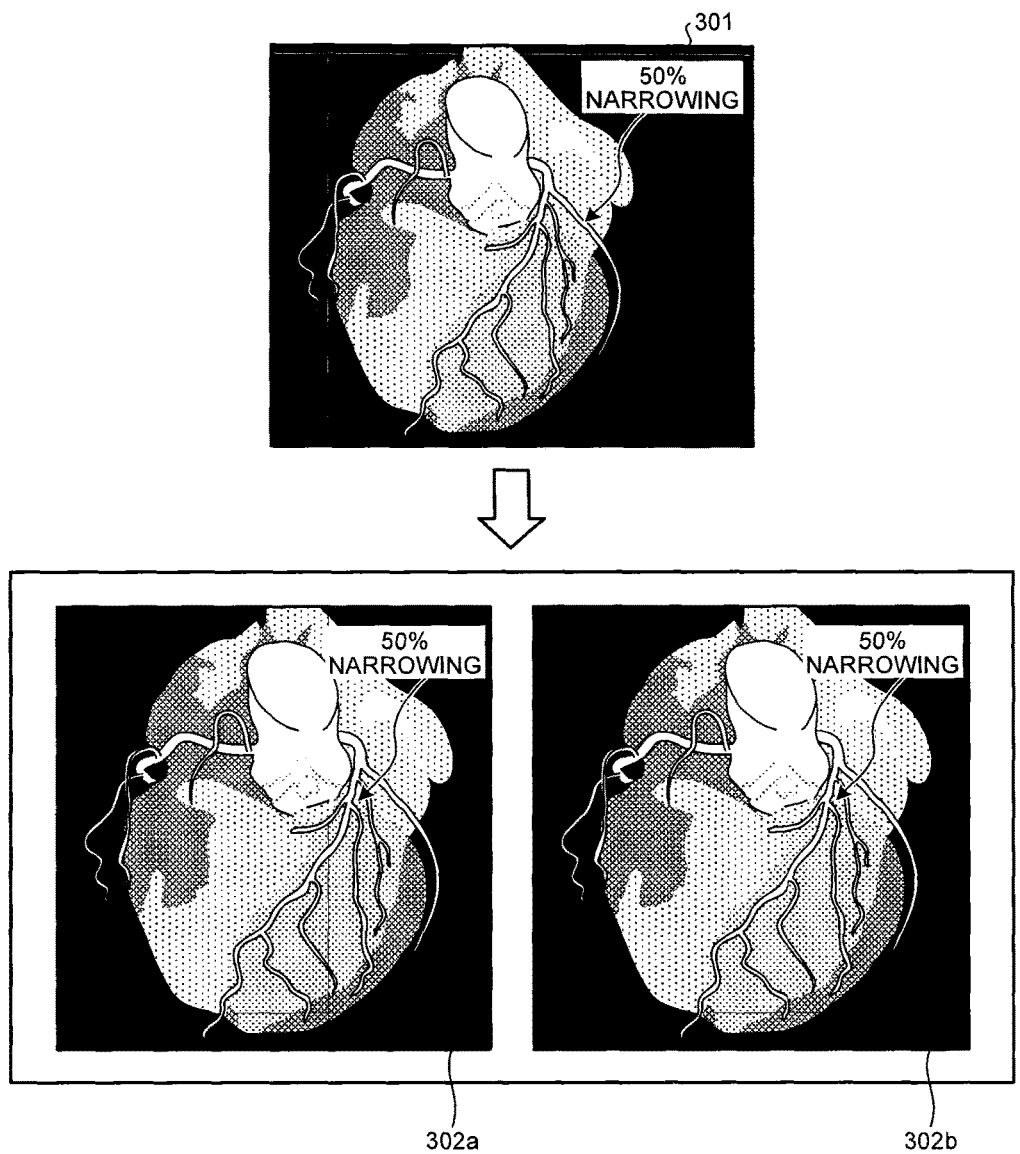
FIG. 8 is a schematic of parallax images output by an output unit according to the first embodiment.

If the determination unit 1353 determines that the parallax number is one, for example, the output unit 1354 outputs, as parallax images of the parallax number, an image in which two parallax images are arranged side by side as a captured image among the parallax images stored by the storing unit 1352 as the captured images. FIG. 8 is a schematic of parallax images output by the output unit according to the first embodiment. In FIG. 8, an explanation will be made of the case where the storing unit 1352 stores nine parallax images used for displaying a stereoscopic image 301 as the captured images. In this case, the output unit 1354 selects two parallax images 302a and 302b from the nine parallax images by an arbitrary method, and arranges the parallax images thus selected side by side to output the parallax images. As a result, by causing the user to see one and the other of the parallax images with the left eye and the right eye, respectively, the user can view a two-parallax stereoscopic image. In other words, the output unit 1354 outputs captured images for stereo vision capable of being viewed by an ordinary monitor. The captured image to be output when the determination unit 1353 determines that the parallax number is one is not limited to an image in which two parallax images are arranged side by side. Alternatively, one arbitrary parallax image may be output as the captured image.

If the determination unit 1353 determines that the parallax number is two, for example, the output unit 1354 selects two parallax images by an arbitrary method from the parallax images stored by the storing unit 1352 as the captured images, and outputs the two parallax images thus selected as the captured image.

More specifically, the output unit 1354 selects two parallax images at a parallactic angle of 5 to 6 degrees, and outputs the two parallax images thus selected as the captured image, for example. Furthermore, an explanation will be made of the case where parallax images to be selected when the parallax number is two are specified in advance and information indicating the parallax images to be selected is associated with the captured images by an arbitrary method. In this case, the output unit 1354 may select and output the two parallax images specified in advance.

An explanation will be made of the meaning of outputting two parallax images at a parallactic angle of 5 to 6 degrees as captured images. Causing the user to see one and the other of the parallax images at a parallactic angle of 5 to 6 degrees with the left eye and the right eye, respectively, facilitates the user's viewing a three-dimensional stereoscopic image. Based on this, the output unit 1354 outputs two parallax images at a parallactic angle of 5 to 6 degrees as captured images. In other words, the difference of parallactic angles between the parallax images stored by the storing unit 1352 as the captured images differs depending on setting of the rendering conditions for generating the parallax images. As a result, not by outputting two arbitrary parallax images among the parallax images stored as the captured images, but by outputting two parallax images at a parallactic angle of 5 to 6 degrees, the user can view a two-parallax stereoscopic image reliably.

The meaning of processing performed by each unit of the control unit 135 will now be described. The number of parallax images stored in a predetermined storage unit as captured images for a stereoscopic image differs depending on stereoscopic images being displayed on the workstation 130 and the terminal device 140. If a nine-parallax stereoscopic image is being displayed to the user without glasses, for example, the storing unit 1352 stores nine parallax images as captured images. By contrast, if a two-parallax stereoscopic image is being displayed to the user without glasses, for example, the storing unit 1352 stores two parallax images as captured images. In other words, the number of parallax images to be stored by the storing unit 1352 as captured images differs depending on stereoscopic images.

There are various types of display devices serving as the destination of the captured images. Examples of the display device include a display device that can display a stereoscopic image and a display device that fails to display a stereoscopic image. Furthermore, as described above, examples of the display device that can display a stereoscopic image include a device that displays a two-parallax stereoscopic image (binocular parallax images) to the user who wears a specific device, such as a pair of stereoscopic vision glasses and a device that displays a nine-parallax stereoscopic image to the user without glasses by using a beam control element, such as a lenticular lens. In other words, the number of parallax images to be displayed differs depending on display devices serving as the destination of the captured images.

As described above, the number of parallax images to be stored by the storing unit 1352 as captured images differs depending on stereoscopic images, and the number of parallax images to be displayed also differs depending on display devices serving as the destination of the captured images. Based on this, the storing unit 1352 temporarily stores all the parallax images used for displaying a stereoscopic image being displayed by the workstation 130 and the terminal device 140. To output captured images in this state, the determination unit 1353 determines the parallax number of an image to be displayed by the display device serving as the destination of the captured images. Subsequently, parallax images of the parallax number determined by the determination unit 1353 are selected, and the output unit 1354 outputs the parallax images thus selected. As a result, the captured images can be output in a manner suitable for the display device serving as the destination of the captured images. If the display device serving as the destination of the captured images can display a stereoscopic image to the user, for example, it is possible to output a plurality of parallax images as the captured images. By contrast, if the display device serving as the destination of the captured images fails to display a stereoscopic image to the user, for example, it is possible to allow the user to view a stereoscopic image by outputting one parallax image as the captured image or by outputting an image in which two parallax images are arranged side by side.

In other words, as illustrated in the stereoscopic image 301 in FIG. 8, if an arrow is placed at a narrowed position in a heart and character information of "50% narrowing" is displayed on a nine-parallax stereoscopic image, for example, it is possible to output a captured image on which the arrow is placed at the narrowed position in the heart and the character information of "50% narrowing" is displayed to any type of display device serving as the destination of the captured image.

In terms of the captured image to be output, explanations will be made of the case where each of the parallax images integrated with each of the overlay images is stored as a captured image, the case where each of the parallax images is stored in a manner associated with each of the overlay images, and the case where each of the parallax images is stored in a manner associated with additional information.

An explanation will be made of the case where each of the parallax images integrated with each of the overlay images is stored as a captured image. In this case, the arrow is already placed at the narrowed position in the heart and the character information of "50% narrowing" is already displayed on each of the parallax images stored as the captured image. As a result, it is possible to output the captured image on which the arrow is placed at the narrowed position in the heart and the character information of "50% narrowing" is displayed to any type of display device serving as the destination of the captured images.

An explanation will be made of the case where each of the parallax images is stored in a manner associated with each of the overlay images. In this case, an overlay image for displaying the arrow indicating the narrowed position in the heart and the character information of "50% narrowing" is associated with each of the parallax images stored as the captured image. As a result, the output unit 1354 outputs the parallax image thus selected and the overlay image associated with the parallax image thus selected in a manner associated with each other, thereby making it possible to output the captured image on which the arrow is placed at the narrowed position in the heart and the character information of "50% narrowing" is displayed.

An explanation will be made of the case where each of the parallax images is stored in a manner associated with additional information. In this case, by superimposing an overlay image generated based on the additional information on each of the parallax images to output each of the parallax images, it is possible to output the captured image on which the arrow is placed at the narrowed position in the heart and the character information of "50% narrowing" is displayed. Furthermore, by outputting the additional information without any change, it is possible to output the additional information as text information indicating an annotation.

Processing According to the First Embodiment

Figure 9:
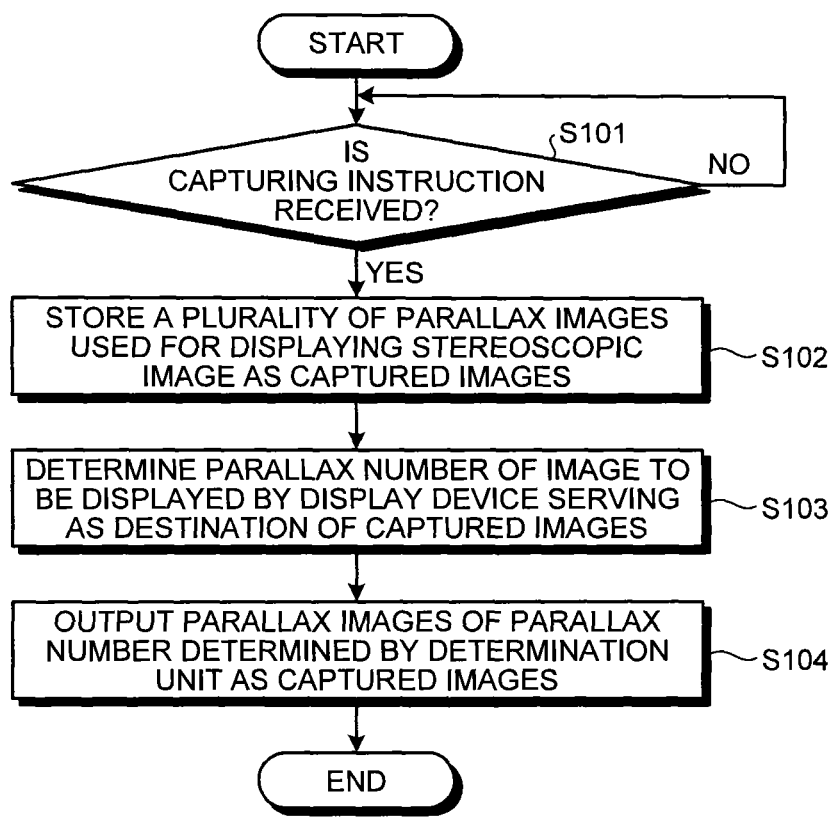
FIG. 9 is a flow chart of an exemplary flow of processing performed by an image processing apparatus according to the first embodiment.

An exemplary flow of processing performed by the workstation 130 according to the first embodiment will be described with reference to FIG. 9. FIG. 9 is a flow chart of an exemplary flow of processing performed by the image processing apparatus according to the first embodiment. In the example illustrated in FIG. 9, while an explanation will be made of the flow of processing in which an output instruction is received after a capturing instruction is received, it is not limited thereto. Alternatively, for example, the flow of processing in which a capturing instruction is received may be separated from the flow of processing in which an output instruction is received.

As illustrated in FIG. 9, if the reception unit 1351 in the workstation 130 receives a capturing instruction (Yes at Step S101), the storing unit 1352 stores a plurality of parallax images used for displaying a stereoscopic image in a manner associated with one another as captured images (Step S102). If nine parallax images used for displaying a stereoscopic image are present, for example, the storing unit 1352 stores the nine parallax images in a manner associated with one another as captured images.

Subsequently, if the reception unit 1351 receives an output instruction, the determination unit 1353 determines the parallax number of an image to be displayed by a display device serving as a destination of the captured images (Step S103). The determination unit 1353 determines that the parallax number is nine, two, or one, for example.

The output unit 1354 then outputs parallax images of the parallax number determined by the determination unit 1353 as captured images among the parallax images stored by the storing unit 1352 as the captured images (Step S104). If the determination unit 1353 determines that the parallax number is two, for example, the output unit 1354 outputs two parallax images as captured images.

Advantageous Effects According to the First Embodiment

As described above, according to the first embodiment, if a capturing instruction to capture a stereoscopic image being displayed on the workstation 130 and the terminal device 140 is received, a plurality of parallax images used for displaying the stereoscopic image being displayed are stored in a manner associated with one another as captured images in a predetermined storage device. As a result, it is possible to capture the stereoscopic image. Specifically, even in a state where various types of display devices are supposed to be a destination of the captured images, it is possible to store the captured images compatible with the various types of display devices.

According to the first embodiment, if a stereoscopic image is displayed by displaying the parallax images on which overlay images for displaying an annotation are superimposed, the storing unit 1352 integrates each of the parallax images with each of the overlay images superimposed on each of the parallax images, and stores each of the parallax images integrated with each of the overlay images as a captured image. As a result, it is possible to reliably store the parallax images used for displaying the stereoscopic image being actually displayed.

According to the first embodiment, the storing unit 1352 stores each of the parallax images and each of the overlay images superimposed on each of the parallax images in a manner associated with each other as a captured image. As a result, if the captured image is output in response to an output instruction, the display device serving as the destination can display the parallax images on which the overlay images are superimposed or the parallax images on which no overlay image is superimposed.

According to the first embodiment, the reception unit 1351 further receives an output instruction to output the captured images stored by the storing unit 1352, and the determination unit 1353 determines the parallax number of an image to be displayed by the display device serving as the destination of the captured images. Subsequently, the output unit 1354 outputs parallax images of the parallax number determined by the determination unit 1353 as captured images among the parallax images stored by the storing unit 1352 as the captured images. As a result, it is possible to output the captured images capable of being displayed by the display device serving as the destination of the captured images.

In other words, a monitor capable of displaying a stereoscopic image can display a stereoscopic image providing a sense of depth. Examples of the monitor capable of displaying a stereoscopic image include a plurality of types of monitors (e.g., a polarizing glasses method, a shutter glasses method, and a naked eye method), and the stereoscopic effect sensed by the user differs depending on the monitors. In other words, an image obtained by screen capturing on a typical monitor that displays no stereoscopic image is also displayed on another typical monitor that displays no stereoscopic image. By contrast, a monitor capable of displaying a stereoscopic image is assumed to fail to perform screen capturing because there is a plurality of methods for displaying a stereoscopic image.

Based on this, according to the first embodiment, the parallax images used for displaying a stereoscopic image are stored in a manner associated with one another as captured images, and parallax images of the parallax number for the display device serving as the destination are output. As a result, it is possible to store and output the captured images regardless of the method employed by the monitor capable of displaying a stereoscopic image.

According to the first embodiment, if the determination unit 1353 determines that the parallax number is two, the output unit 1354 outputs two parallax images at a parallactic angle of 5 to 6 degrees as captured images among the parallax images stored by the storing unit 1352 as the captured images. As a result, it is possible to display a stereoscopic image that facilitates stereoscopic vision to the user.

According to the first embodiment, if the determination unit 1353 determines that the parallax number is one, the output unit 1354 outputs an image in which two parallax images are arranged side by side as a captured image among the parallax images stored by the storing unit 1352 as the captured images. As a result, even a display device whose parallax number is one can display a stereoscopic image to the user.

Second Embodiment

The first embodiment has been described above, but various forms of embodiments, which is different from the first embodiment, can be embodied.

Additional Information

If each of the parallax images is stored in a manner associated with additional information as a captured image and the determination unit 1353 determines that the parallax number is one, for example, the output unit 1354 may delete information on the depth from the additional information to output the parallax images. The output unit 1354, for example, may delete the additional information to output the parallax images. Furthermore, the output unit 1354 may select and output an arbitrary parallax image from the parallax images, or may select two parallax images and output the parallax images thus selected in a manner arranged side by side.

An explanation will be made of the case where the display device serving as the destination of the captured images displays no stereoscopic image and setting of coordinates of a start point and an end point of an arrow is stored as the additional information. In this case, how the display device processes the information on the depth depends on the display device. Based on this, by deleting the values of coordinates in the depth direction among settings of the coordinates stored as the additional information, or by changing the values to "0", for example, it is possible to reduce the possibility that an error occurs because of processing performed by the display device. The information on the depth corresponds to the value in the z-axis direction indicating the depth among the information indicating the direction of the arrow, for example.

Additional Information

If the storing unit 1352 stores each of the parallax images in a manner associated with additional information as a captured image, for example, the storing unit 1352 may store a flag indicating whether to delete the additional information in the case where the display device serving as the destination does not perform stereoscopic display in a manner associated with the captured image. If the user inputs setting information for displaying an annotation together with information indicating that the additional information can be deleted in the case where the display device serving as the destination does not perform stereoscopic display, for example, the storing unit 1352 stores each of the parallax images in a manner associated with the additional information as a captured image, and stores a flag in a manner associated with the captured image. Examples of the annotation that can be deleted in the case where the display device serving as the destination does not perform stereoscopic display include characters of "being displayed stereoscopically" and a scale in the depth direction used for indicating the magnitude of the sense of depth and of the stereoscopic effect during stereoscopic display.

In this case, if the determination unit 1353 determines that the parallax number is one, the output unit 1354 determines whether a flag is set. If a flag is determined to be set, the output unit 1354 deletes the additional information from the captured image to output the captured image. The output unit 1354, for example, outputs an arbitrary parallax image among the parallax images.

Overlay Image

If the output unit 1354 outputs a parallax image associated with an overlay image as a captured image, for example, the display device serving as the destination may superimpose the overlay image on the parallax image to display the parallax image, or may display the parallax image without superimposing the overlay image thereon. The display device serving as the destination may receive selection of whether to superimpose the overlay image from the user. If the display device serving as the destination superimposes the overlay image on the parallax image to display the parallax image, the display device may also output a message indicating that the overlay image is superimposed.

Image Storage

The storage in which the parallax images used for displaying a stereoscopic image are stored in a manner associated with one another as captured images may be a portable storage medium, for example. The parallax images may be stored in a manner associated with one another in a portable storage medium, such as an external hard disc, a flash memory, a memory card, a flexible disc (FD), a compact disc read-only memory (CD-ROM), a magneto-optical disc (MO), and a digital versatile disc (DVD), or the parallax images may be stored in a manner further associated with an annotation, for example.

System Configuration

Among the processing explained in the present embodiments, all or a part of the processing explained as processing performed automatically may be performed manually. Alternatively, all or a part of the processing explained as processing performed manually may be performed automatically by a known method. In addition, the operating process, the control process, the specific names, and the information including various types of data and parameters described in the description and the drawings (FIG. 1 to FIG. 9) can be changed arbitrarily if not otherwise specified.

The components of the devices are functionally conceptually illustrated, and are not necessarily configured physically as illustrated in the drawings. In other words, the specific aspect of dispersion and integration of the devices is not limited to the aspect illustrated in the drawings, and the whole or a part of the devices may be configured by being dispersed or integrated in arbitrary units functionally or physically depending on various types of loads and usages.

The control unit 135 of the workstation 130 may be connected via a network as an external device of the workstation 130, for example.

Others

The image processing program explained in the present embodiments can be distributed via a network, such as the Internet. Furthermore, the image processing program may be recorded in a computer-readable recording medium, such as a hard disc, an FD, a CD-ROM, an MO, and a DVD, and may be executed by being read from the recording medium by a computer.

Advantageous Effects of the Embodiments

The image processing apparatus according to at least one of the embodiments receives a capturing instruction to capture a stereoscopic image being displayed stereoscopically, and stores a plurality of parallax images used for displaying the stereoscopic image being displayed stereoscopically in a manner associated with one another as captured images in a predetermined storage device, thereby making it possible to capture the stereoscopic image.

The image processing apparatus according to the embodiments receives a capturing instruction to capture a stereoscopic image being displayed stereoscopically, and stores a plurality of parallax images used for displaying the stereoscopic image being displayed stereoscopically in a manner associated with one another as captured images in a predetermined storage device, thereby making it possible to capture the stereoscopic image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
processing circuitry configured to receive a capturing instruction to capture a stereoscopic image being displayed stereoscopically; and
storing circuitry configured to, when the processing circuitry receives the capturing instruction, store a plurality of parallax images used for displaying the stereoscopic image being displayed by a stereoscopic image display device in a manner associated with one another as a captured image in a predetermined storage device,
wherein the storing circuitry is configured to store additional information that is information for generating an overlay image for displaying an annotation and each of the parallax images in the plurality of parallax images in a manner associated with each other as the captured image; and
the processing circuitry is configured
to further receive an output instruction to output the captured image stored by the storing circuitry to a first display device for displaying image of a predetermined parallax number or a second display device for displaying image of different parallax number from the predetermined parallax number,
to determine the parallax number of the image to be displayed by the first display device or the parallax number of the image to be displayed by the second display device based on the display device of the output destination specified by the output instruction,
to select parallax images of the same number as the determined parallax number from the parallax images stored by the storing circuitry as the captured image, and
to output the selected parallax images to the first display device or the second display device as the captured image based on the display device of the output destination specified by the output instruction, wherein
the processing circuitry is configured to, when the parallax number is two, select two parallax images at a parallactic angle of 5 to 6 degrees from the parallax images stored by the storing circuitry as the captured image and to output the two parallax images thus selected as the captured image.

2. The image processing apparatus according to claim 1, wherein
the stereoscopic image is displayed by displaying each of the parallax images on which the overlay image for displaying the annotation is superimposed, and
the storing circuitry is configured to integrate the overlay image superimposed on each of the parallax images with each of the parallax images and to store each of the parallax images integrated with the overlay image as the captured image.

3. The image processing apparatus according to claim 1, wherein
the stereoscopic image is displayed by displaying each of the parallax images on which the overlay image for displaying the annotation is superimposed, and
the storing circuitry is configured to store each of the parallax images and the overlay image superimposed on each of the parallax images in a manner associated with each other as the captured image.

4. The image processing apparatus according to claim 1, wherein the predetermined storage device is a portable storage device.

5. An image processing apparatus comprising:
processing circuitry configured to receive a capturing instruction to capture a stereoscopic image being displayed stereoscopically; and
storing circuitry configured to, when the processing circuitry receives the capturing instruction, store a plurality of parallax images used for displaying the stereoscopic image being displayed by a stereoscopic image display device in a manner associated with one another as a captured image in a predetermined storage device, wherein
the storing circuitry is configured to store additional information that is information for generating an overlay image for displaying an annotation and each of the parallax images in the plurality of parallax images in a manner associated with each other as the captured image; and
the processing circuitry is configured
to further receive an output instruction to output the captured image stored by the storing circuitry to a first display device for displaying image of a predetermined parallax number or a second display device for displaying image of different parallax number from the predetermined parallax number,
to determine the parallax number of the image to be displayed by the first display device or the parallax number of the image to be displayed by the second display device based on the display device of the output destination specified by the output instruction, to select parallax images of the same number as the determined parallax number from the parallax images stored by the storing circuitry as the captured image, and to output the selected parallax images to the first display device or the second display device as the captured image based on the display device of the output destination specified by the output instruction, wherein the processing circuitry is configured to, when the parallax number is one, select, as parallax images of the parallax number, two parallax images from the parallax images stored by the storing circuitry as the captured image and to output the parallax images in a manner arranged side by side.

6. The image processing apparatus according to claim 5, wherein the stereoscopic image is displayed by displaying each of the parallax images on which the overlay image for displaying the annotation is superimposed, and the storing circuitry is configured to integrate the overlay image superimposed on each of the parallax images with each of the parallax images and to store each of the parallax images integrated with the overlay image as the captured image.

7. The image processing apparatus according to claim 5, wherein the stereoscopic image is displayed by displaying each of the parallax images on which the overlay image for displaying the annotation is superimposed, and the storing circuitry is configured to store each of the parallax images and the overlay image superimposed on each of the parallax images in a manner associated with each other as the captured image.

8. The image processing apparatus according to claim 5, wherein the predetermined storage device is a portable storage device.

9. An image processing apparatus comprising:

processing circuitry configured to receive a capturing instruction to capture a stereoscopic image being displayed stereoscopically; and storing circuitry configured to, when the processing circuitry receives the capturing instruction, store a plurality of parallax images used for displaying the stereoscopic image being displayed by a stereoscopic image display device in a manner associated with one another as a captured image in a predetermined storage device, wherein the storing circuitry is configured to store additional information that is information for generating an overlay image for displaying an annotation and each of the parallax images in the plurality of parallax images in a manner associated with each other as the captured image; and the processing circuitry is configured to further receive an output instruction to output the captured image stored by the storing circuitry to a first display device for displaying image of a predetermined parallax number or a second display device for displaying image of different parallax number from the predetermined parallax number, to determine the parallax number of the image to be displayed by the first display device or the parallax number of the image to be displayed by the second display device based on the display device of the output destination specified by the output instruction, to select parallax images of the same number as the determined parallax number from the parallax images stored by the storing circuitry as the captured image, and to output the selected parallax images to the first display device or the second display device as the captured image based on the display device of the output destination specified by the output instruction, wherein the processing circuitry is configured to, when each of the parallax images is stored in a manner associated with the additional information as the captured image and the parallax number is one, delete information on depth from the additional information and to output the parallax images.

10. The image processing apparatus according to claim 9, wherein the stereoscopic image is displayed by displaying each of the parallax images on which the overlay image for displaying the annotation is superimposed, and the storing circuitry is configured to integrate the overlay image superimposed on each of the parallax images with each of the parallax images and to store each of the parallax images integrated with the overlay image as the captured image.

11. The image processing apparatus according to claim 9, wherein the stereoscopic image is displayed by displaying each of the parallax images on which the overlay image for displaying the annotation is superimposed, and the storing circuitry is configured to store each of the parallax images and the overlay image superimposed on each of the parallax images in a manner associated with each other as the captured image.

12. The image processing apparatus according to claim 9, wherein the predetermined storage device is a portable storage device.

13. An image processing method comprising:

receiving a capturing instruction to capture a stereoscopic image being displayed stereoscopically;

storing, when the capturing instruction is received, a plurality of parallax images used for displaying the stereoscopic image being displayed by a stereoscopic image display device in a manner associated with one another as a captured image in a predetermined storage device;

storing additional information that is information for generating an overlay image for displaying an annotation acquired and each of the parallax images in the plurality of parallax images in a manner associated with each other as the captured image;

receiving an output instruction to output the captured image stored by the storing circuitry to a first display device for displaying image of a predetermined parallax number or a second display device for displaying image of different parallax number from the predetermined parallax number;

determining the parallax number of the image to be displayed by the first display device or the parallax number of the image to be displayed by the second display device based on the display device of the output destination specified by the output instruction;

selecting parallax images of the same number as the determined parallax number from the parallax images stored by the storing circuitry as the captured image;

outputting the selected parallax images to the first display device or the second display device as the captured image based on the display device of the output destination specified by the output instruction; and when the parallax number is two, selecting two parallax images at a parallactic angle of 5 to 6 degrees from the parallax images stored by the storing circuitry as the captured image and to output the two parallax images thus selected as the captured image.

14. An image processing method comprising:

receiving a capturing instruction to capture a stereoscopic image being displayed stereoscopically;

storing, when the capturing instruction is received, a plurality of parallax images used for displaying the stereoscopic image being displayed by a stereoscopic image display device in a manner associated with one another as a captured image in a predetermined storage device;

storing additional information that is information for generating an overlay image for displaying an annotation acquired and each of the parallax images in the plurality of parallax images in a manner associated with each other as the captured image;

receiving an output instruction to output the captured image stored by the storing circuitry to a first display device for displaying image of a predetermined parallax number or a second display device for displaying image of different parallax number from the predetermined parallax number;

determining the parallax number of the image to be displayed by the first display device or the parallax number of the image to be displayed by the second display device based on the display device of the output destination specified by the output instruction;

selecting parallax images of the same number as the determined parallax number from the parallax images stored by the storing circuitry as the captured image;

outputting the selected parallax images to the first display device or the second display device as the captured image based on the display device of the output destination specified by the output instruction; and when the parallax number is one, selecting, as parallax images of the parallax number, two parallax images from the parallax images stored by the storing circuitry as the captured image and to output the parallax images in a manner arranged side by side.

15. An image processing method comprising:

receiving a capturing instruction to capture a stereoscopic image being displayed stereoscopically;

storing, when the capturing instruction is received, a plurality of parallax images used for displaying the stereoscopic image being displayed by a stereoscopic image display device in a manner associated with one another as a captured image in a predetermined storage device;

storing additional information that is information for generating an overlay image for displaying an annotation acquired and each of the parallax images in the plurality of parallax images in a manner associated with each other as the captured image;

receiving an output instruction to output the captured image stored by the storing circuitry to a first display device for displaying image of a predetermined parallax number or a second display device for displaying image of different parallax number from the predetermined parallax number;

determining the parallax number of the image to be displayed by the first display device or the parallax number of the image to be displayed by the second display device based on the display device of the output destination specified by the output instruction;

selecting parallax images of the same number as the determined parallax number from the parallax images stored by the storing circuitry as the captured image;

outputting the selected parallax images to the first display device or the second display device as the captured image based on the display device of the output destination specified by the output instruction; and when each of the parallax images is stored in a manner associated with the additional information as the captured image and the parallax number is one, deleting information on depth from the additional information and outputting the parallax images.

16. A medical image diagnosis apparatus comprising:

processing circuitry configured to receive a capturing instruction to capture a stereoscopic image being displayed stereoscopically; and storing circuitry configured to, when the processing circuitry receives the capturing instruction, store a plurality of parallax images used for displaying the stereoscopic image being displayed by a stereoscopic image display device in a manner associated with one another as a captured image in a predetermined storage device, wherein the storing circuitry is configured to store additional information that is information for generating an overlay image for displaying an annotation and each of the parallax images in the plurality of parallax images in a manner associated with each other as the captured image; and the processing circuitry is configured to further receive an output instruction to output the captured image stored by the storing circuitry to a first display device for displaying image of a predetermined parallax number or a second display device for displaying image of different parallax number from the predetermined parallax number, to determine the parallax number of the image to be displayed by the first display device or the parallax number of the image to be displayed by the second display device based on the display device of the output destination specified by the output instruction, to select parallax images of the same number as the determined parallax number from the parallax images stored by the storing circuitry as the captured image, and to output the selected parallax images to the first display device or the second display device as the captured image based on the display device of the output destination specified by the output instruction, wherein the processing circuitry is configured to, when the parallax number is two, select two parallax images at a parallactic angle of 5 to 6 degrees from the parallax images stored by the storing circuitry as the captured image and to output the two parallax images thus selected as the captured image.

17. A medical image diagnosis apparatus comprising:

processing circuitry configured to receive a capturing instruction to capture a stereoscopic image being displayed stereoscopically; and storing circuitry configured to, when the processing circuitry receives the capturing instruction, store a plurality of parallax images used for displaying the stereoscopic image being displayed by a stereoscopic image display device in a manner associated with one another as a captured image in a predetermined storage device, wherein the storing circuitry is configured to store additional information that is information for generating an overlay image for displaying an annotation and each of the parallax images in the plurality of parallax images in a manner associated with each other as the captured image; and the processing circuitry is configured
- to further receive an output instruction to output the captured image stored by the storing circuitry to a first display device for displaying image of a predetermined parallax number or a second display device for displaying image of different parallax number from the predetermined parallax number,
- to determine the parallax number of the image to be displayed by the first display device or the parallax number of the image to be displayed by the second display device based on the display device of the output destination specified by the output instruction,
- to select parallax images of the same number as the determined parallax number from the parallax images stored by the storing circuitry as the captured image, and
- to output the selected parallax images to the first display device or the second display device as the captured image based on the display device of the output destination specified by the output instruction, wherein the processing circuitry is configured to, when the parallax number is one, select, as parallax images of the parallax number, two parallax images from the parallax images stored by the storing circuitry as the captured image and to output the parallax images in a manner arranged side by side.

18. A medical image diagnosis apparatus comprising:

processing circuitry configured to receive a capturing instruction to capture a stereoscopic image being displayed stereoscopically; and storing circuitry configured to, when the processing circuitry receives the capturing instruction, store a plurality of parallax images used for displaying the stereoscopic image being displayed by a stereoscopic image display device in a manner associated with one another as a captured image in a predetermined storage device, wherein the storing circuitry is configured to store additional information that is information for generating an overlay image for displaying an annotation and each of the parallax images in the plurality of parallax images in a manner associated with each other as the captured image; and the processing circuitry is configured
- to further receive an output instruction to output the captured image stored by the storing circuitry to a first display device for displaying image of a predetermined parallax number or a second display device for displaying image of different parallax number from the predetermined parallax number,
- to determine the parallax number of the image to be displayed by the first display device or the parallax number of the image to be displayed by the second display device based on the display device of the output destination specified by the output instruction,
- to select parallax images of the same number as the determined parallax number from the parallax images stored by the storing circuitry as the captured image, and
- to output the selected parallax images to the first display device or the second display device as the captured image based on the display device of the output destination specified by the output instruction, wherein the processing circuitry is configured to, when each of the parallax images is stored in a manner associated with the additional information as the captured image and the parallax number is one, delete information on depth from the additional information and to output the parallax images.

* * * * *